United States Patent
Guo et al.

(10) Patent No.: US 12,319,926 B2
(45) Date of Patent: *Jun. 3, 2025

(54) RECOMBINANT HUMANIZED COLLAGEN TYPE I ALPHA-1 (rhCol1A1), AND EXPRESSION VECTOR AND USE THEREOF

(71) Applicant: Shandong D-Nutrimec Biomedical Co., Ltd., Heze (CN)

(72) Inventors: Zhidong Guo, Heze (CN); Hongwei Ma, Heze (CN); Jiajia Shao, Heze (CN)

(73) Assignee: SHANDONG D-NUTRIMEC BIOMEDICAL CO., LTD., Heze (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/834,523

(22) PCT Filed: Dec. 26, 2023

(86) PCT No.: PCT/CN2023/142064
§ 371 (c)(1),
(2) Date: Jul. 30, 2024

(87) PCT Pub. No.: WO2024/159985
PCT Pub. Date: Aug. 8, 2024

(65) Prior Publication Data
US 2025/0109406 A1   Apr. 3, 2025

(30) Foreign Application Priority Data
Feb. 4, 2023 (CN) .......................... 202310055281.X

(51) Int. Cl.
| | | |
|---|---|---|
| C12N 15/85 | (2006.01) | |
| C07K 14/78 | (2006.01) | |
| C12N 5/00 | (2006.01) | |
| C12N 5/071 | (2010.01) | |
| C12N 15/66 | (2006.01) | |

(52) U.S. Cl.
CPC .............. *C12N 15/85* (2013.01); *C07K 14/78* (2013.01); *C12N 5/0037* (2013.01); *C12N 5/0686* (2013.01); *C12N 15/66* (2013.01); *C12N 2500/02* (2013.01); *C12N 2523/00* (2013.01); *C12N 2527/00* (2013.01); *C12N 2800/107* (2013.01); *C12N 2800/80* (2013.01)

(58) Field of Classification Search
None
See application file for complete search history.

(56) References Cited

FOREIGN PATENT DOCUMENTS

| CN | 101182355 A | 5/2008 |
|---|---|---|
| CN | 101501216 A | 8/2009 |
| CN | 103725622 A | 4/2014 |
| CN | 103725623 A | 4/2014 |
| CN | 108884441 A | 11/2018 |
| CN | 109988243 A | 7/2019 |
| CN | 110606896 A | 12/2019 |
| CN | 111417404 A | 7/2020 |
| CN | 116218864 A | 6/2023 |
| CN | 116333094 A | 6/2023 |

OTHER PUBLICATIONS

Myllyharju et al., "Collagens and collagen-related diseases" 33(1) Annals of Medicine 7-21 (Year: 2001).*
Peng et al., "A novel splicing mutaiton in COL1A1 gene caused type I osteogenesis imperfecta in a Chinese family" 502(2) Gene 168-171 (Year: 2012).*
English Translation of the First Office Action issued for CN Application No. 202310055281.X, issued on Aug. 18, 2023.
English Translation of the First Office Action issued for CN Application No. 202310368832.8, issued on Aug. 12, 2023.
English Translation of the Second Office Action issued for CN Application No. 202310368832.8, issued on Oct. 17, 2023.

* cited by examiner

*Primary Examiner* — Nancy J Leith
(74) *Attorney, Agent, or Firm* — Steven M. Ritchey

(57) ABSTRACT

A recombinant humanized collagen type I alpha-1 (rhCol1A1), and an expression vector and use thereof are provided, belonging to the technical field of bioengineering. The rhCol1A1 has an amino acid sequence of SEQ ID NO: 1. This aim is to solve the problem of difficulty in expressing soluble full-length humanized collagen in *Escherichia coli* prokaryotic expression systems, and differences between the recombinant collagen and humanized collagen in yeast expression systems. It is proposed that the rhCol1A1 chain is expressed in Expi293F™ human embryonic kidney cells, and the protein expression level is increased using a fusion expression plasmid, enabling the expression of full-length humanized collagen type I alpha 1 chain. Activity studies have shown that the expressed rhCol1A1 exhibits a desirable activity in promoting cell migration, and may be widely used in the fields of biomedicine, tissue engineering, skin care, and food.

2 Claims, 2 Drawing Sheets
Specification includes a Sequence Listing.

RECOMBINANT HUMANIZED COLLAGEN TYPE I ALPHA-1 (rhCol1A1), AND EXPRESSION VECTOR AND USE THEREOF

CROSS-REFERENCE TO RELATED APPLICATIONS

This application is a U.S. National Phase application of PCT/CN2023/142064, filed on Dec. 26, 2023, claiming the benefit of Chinese Application No. 202310055281.X, filed on Feb. 4, 2023, both of which are incorporated herein by reference in their entireties.

REFERENCE TO SEQUENCE LISTING

A sequence listing in the file named "ST26 Seqlist TC238479.xml", which is 11,533 bytes (measured in MS-Windows®), contains 4 sequences, and was created on Jun. 25, 2024, is provided herewith via the USPTO's Patent Center, and is incorporated herein by reference in its entirety.

TECHNICAL FIELD

The present disclosure belongs to the field of bioengineering, and specifically relates to a recombinant humanized collagen type I alpha-1 (rhCol1A1), and an expression vector and use thereof.

BACKGROUND

Collagen, as one of the most abundant proteins in mammals (accounting for 25% to 30% of total protein mass), is the main structural protein found in the extracellular matrix of various human connective tissues, and participates in the composition of many human organs and tissues, such as skin, cornea, neural retina, bones, and muscles.

There are currently 28 types of collagen superfamily found, which are roughly divided into fibrillar collagen and non-fibrillar collagen according to the type, structure, and binding of protein chains. A common structural feature of collagens is the presence of a triple helix structure, which has a wide variation. For example, in collagen type I it accounts for 96%, while in collagen type XII it accounts for less than 10%. The peptide chains that make up the triple helix structure are called a chains, and three identical or different peptide chains come together to form homotrimers or heterotrimers. A defining feature of the helical segment in collagen is the presence of Gly-X-Y repetitive sequence in the amino acids, where X and Y are typically proline and 4-hydroxyproline, respectively. This repetitive sequence allows for interchain hydrogen bonding and electrostatic interactions, leading to the formation of stable triple helix structure in collagen.

Collagen has a wide range of application in medicine, skin care, and food. In addition, ongoing research is exploring its potential for cutting-edge applications. For example, a novel MI-RHCMA hydrogel patch made from polygenic recombinant humanized collagen can induce the regeneration of damaged corneal stroma in vivo. Collagen combined with 3D-bioprinting can reconstruct components of the human heart. Biosynthetic corneas made from humanized collagen type III are optically clear and can provide an alternative to donor therapy or genetically-modified pig treatments without the demand for immunosuppressive drugs. Humanized collagen type III can also be used to complete heart valve artificial synthesis and endometrial perfusion repair.

Collagen currently used in industry is mainly extracted from the skin or bones of pigs and cattle, or from the skin of deep-sea fish through acid, alkali or enzymatic methods. Although the technology for extracting collagen from animal tissues is mature, there are problems such as immunogenicity and limited sources, making it difficult to meet the huge market demand.

With the large-scale application of genetic engineering, the generation of recombinant collagen through genetic engineering has become the most promising method to solve the problem of limited collagen sources. Compared with animal-derived collagen, recombinant collagen not only has the advantages of short production cycle, low cost, and suitability for large-scale production, but also avoids problems such as animal protein immunogenicity and animal-derived diseases. Therefore, the preparation of recombinant collagen, especially recombinant humanized collagen, is currently a hot topic in collagen production research.

Due to the large molecular weight (generally greater than 100 kDa) and various protein post-translational modifications such as proline and lysine hydroxylation as well as glycosylation, soluble full-length humanized collagen is difficult to be expressed in the *Escherichia coli* prokaryotic expression system with existing technologies. In the yeast expression system, the differences in protein post-translational modification between yeast and human result in a recombinant collagen that is quite different from humanized collagen.

SUMMARY

In view of the above situation, in order to overcome the shortcomings of the existing technology, the present disclosure provides methods of plasmid construction, expression, and use of a recombinant humanized collagen type I alpha-1 (rhCol1A1). This process is designed to solve the problem of difficulty in expressing soluble full-length humanized collagen in an *Escherichia coli* prokaryotic expression system, and differences between the recombinant collagen and humanized collagen in a yeast expression system. It is proposed that an rhCol I α1 chain is expressed in human embryonic kidney cells Expi293F™, and the protein expression level is increased using a fusion expression plasmid, enabling the expression of a full-length segment of the humanized collagen type I α1 chain. The obtained recombinant protein sequence is close to the humanized collagen type I α1 chain (three more amino acids at the N-terminus), and has low immunogenicity and high safety. Activity studies have shown that the rhCol1A1 expressed in the present disclosure has a desirable activity in promoting the cell migration and exhibits a huge application potential.

Technical Solutions for Resolving the Technical Problem

A first objective of the present disclosure is to provide an rhCol1A1, where the rhCol1A1 has an amino acid sequence of in SEQ ID NO: 1.

In some embodiments, the amino acid sequence of rhCol1A1 includes an amino acid sequence of a secretion signal peptide from *Trypanosoma cruzi* (*T. cruzi*) α-mannosidase, an amino acid sequence of green fluorescent protein (GFP), a sequence of tobacco etch virus (TEV) protease cleavage site, and an amino acid sequence at positions 162 to 1,218 of a humanized collagen type I α1 chain.

In some embodiments, the amino acid sequence at positions 162 to 1,218 of the humanized collagen type I α1 chain is set forth in SEQ ID NO: 2; a DNA sequence at positions 162 to 1,218 of the humanized collagen type I α1 chain is set forth in SEQ ID NO: 3; proteins expressed by humanized cells have a variety of post-translational modifications, such that the humanized collagen type I α1 chain has a molecular weight of 138 kDa.

In some embodiments, the amino acid sequence of the secretion signal peptide from *T. cruzi* α-mannosidase, the amino acid sequence of GFP, and the sequence of TEV protease cleavage site are encoded by a DNA sequence of SEQ ID NO: 4 directly ligated to the sequence of SEQ ID NO: 3.

A second objective of the present disclosure is to provide an expression vector of rhCol1A1, including nucleotide sequences of rhCol1A1 and a basic vector pcDNA3.1.

In a further embodiment, a method of expression using the expression vector includes transfecting the expression vector of rhCol1A1 into host cells to allow expression.

In some embodiments, the host cells are Expi293F™ human embryonic kidney cells.

In a further embodiment, a method for expressing the rhCol I includes the following steps:

(1) plasmid extraction: transforming the expression vector into *Escherichia coli* (*E. coli*) DH5α, inoculating the transformed *E. coli* DH5α into a first Luria-Bertani (LB) broth to allow incubation at 37° C. and 200 rpm for 30 min; spreading a solution of the transformed *E. coli* DH5α on an LB agar plate to allow incubation upside down in an incubator at 37° C. for 12 h; and selecting a single positive colony, which is then added into 50 mL of a second LB broth to allow incubation at 37° C. and 200 rpm for 12 h to extract a plasmid;

(2) protein expression: subjecting the Expi293F™ human embryonic kidney cells to pre-suspension culture in a serum-free medium on a shaker at 37° C., 110 rpm, with 80% humidity, and 7% carbon dioxide; conducting cell transfection when a cell density reaches $(1.5\text{-}2.5)\times10^6$ cells/mL and a cell viability of greater than 95%; where the cell transfection includes the following steps: adding a transfection reagent to a first cell medium and mixing gently to obtain a solution A; adding the plasmid obtained in step (1) to a second cell medium and mixing gently to obtain a solution B; adding the solution B into the solution A, mixing gently, and allowing to stand for 15 min; and adding a mixture of the solution A and the solution B into the suspension cultured Expi293F™ human embryonic kidney cells, and continuing culture for 6 d to 7 d; when a cell viability reaches lower than 50%, collecting obtained cells to obtain a cell suspension;

(3) protein purification: centrifuging the cell suspension obtained in step (2) at 11,000 rpm for 10 min at 4° C., incubating an obtained supernatant with a nickel column, eluting by gravity, washing the nickel column with 50 mL of a PBS solution containing 10 mM imidazole, gradient-eluting with PBS solutions containing 30 mM, 50 mM, 100 mM, 200 mM, and 300 mM imidazole separately, and detecting protein by sodium dodecyl sulfate-polyacrylamide gel electrophoresis (SDS-PAGE); combining obtained eluate, and removing the imidazole by an ultrafiltration tube to obtain purified protein; and (4) GFP fusion protein excision: adding the purified protein into an enzyme reaction solution, adding 50 U of an enzyme solution to allow a reaction overnight at 4° C., incubating a resulting protein solution with a nickel column to remove tag protein and the enzyme to obtain target protein rhCol1A1.

A third objective of the present disclosure is to provide use of the rhCol1A1, where the rhCol1A1 is used in studying promotion of mouse embryonic fibroblast migration.

Compared with the prior art, the embodiments of the present disclosure have the following beneficial technical effects:

This process is designed to solve the problem of difficulty in expressing soluble full-length humanized collagen in an *Escherichia coli* prokaryotic expression system, and differences between the recombinant collagen and humanized collagen in the yeast expression system. It is proposed that an rhCol I α1 chain is expressed in Expi293F™ human embryonic kidney cells, and a protein expression level is increased using a fusion expression plasmid, enabling the expression of the full-length segment of the humanized collagen type I α1 chain. The obtained recombinant protein sequence is close to the humanized collagen type I α1 chain (three more amino acids at the N-terminus).

In the present disclosure, the amino acid sequence at positions 162-1218 of the humanized collagen type I α1 chain is selected and ligated to a vector pcDNA3.1. A secretion signal peptide, fusion protein (GFP), and TEV protease cleavage site are added to the N-terminus of the target protein to optimize the expression vector. The secretion signal peptide can transport the gene-expressed recombinant protein into cell medium and increase the expression level of the recombinant protein. The fusion protein GFP enhances the ability of the recombinant protein in resisting chemical denaturants, improves folding kinetics of the recombinant protein, and facilitates the production of active recombinant proteins. The TEV protease cleavage site can be recognized and cleaved by TEV cysteine protease, and the fusion protein can be removed to obtain a tag-free target recombinant protein that is close to the humanized collagen sequence, thereby improving the safety of the recombinant protein.

The optimized expression vector is transfected into Expi293F™ human embryonic kidney cells to secrete and express soluble GFP-fused rhCol1A1. Under the same expression conditions, no expression of soluble recombinant protein is detected using the GFP-free expression vector. The GFP is conducive to the correct folding of high-molecular-weight proteins and improves the expression level of active proteins. GFP protein is expressed in fusion via a plasmid to increase protein expression. TEV protease excises the fusion protein GFP to obtain rhCol1A1, thereby achieving the expression and production of recombinant humanized collagen with a larger molecular weight.

In the present disclosure, the rhCol1A1 is an active recombinant protein. Activity studies show that the rhCol1A1 promotes cell migration in BALB/c 3T3 cells, with 12 h scratch recovery rates of 58.1% (10 μg/mL) and 98.6% (100 μg/mL), respectively, much higher than 38.2% (0 μg/mL) of the control group.

DETAILED DESCRIPTION OF THE EMBODIMENTS

Figure 1:
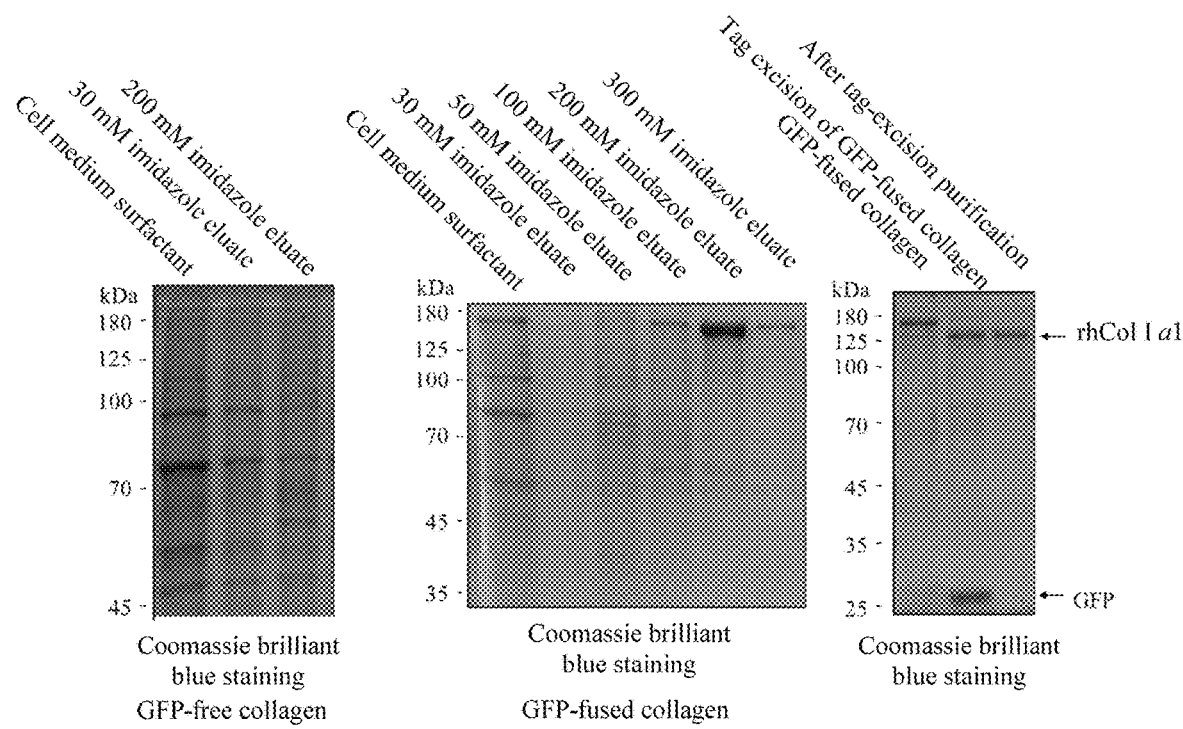
FIG. 1 shows an SDS-PAGE electrophoresis pattern of the rhCol1A1.

The technical solutions in the embodiments of the present disclosure are clearly and completely described below with reference to the accompanying drawings in the examples of the present disclosure. Apparently, the described examples are merely a part rather than all of the embodiments of the present disclosure. All other embodiments derived from the examples in the present disclosure by a person of ordinary skill in the art without creative efforts should fall within the protection scope of the present disclosure.

Unless otherwise defined, all professional and scientific terms used herein have the same meaning as familiar to those skilled in the art. In addition, any methods and materials similar or equivalent to those described can be used in the methods of the present disclosure. Preferred methods and materials for implementation herein are for illustrative purposes only, but do not limit the content of the present disclosure.

The present disclosure provides an rhCol1A1, where the rhCol1A1 has an amino acid sequence of SEQ ID NO: 1, and the rhCol1A1 has a molecular weight of 95 kDa.

In the present disclosure, the amino acid sequence of the rhCol1A1 includes an amino acid sequence of a secretion signal peptide from $T.$ $cruzi$ $\alpha$-mannosidase, an amino acid sequence of green fluorescent protein (GFP), a sequence of tobacco etch virus (TEV) protease cleavage site, and an amino acid sequence at positions 162 to 1,218 of a humanized collagen type I $\alpha$1 chain.

In the present disclosure, the amino acid sequence at positions 162 to 1,218 of the humanized collagen type I $\alpha$1 chain is set forth in SEQ ID NO: 2; a DNA sequence on the positions 162 to 1,218 of the humanized collagen type I $\alpha$1 chain is set forth in SEQ ID NO: 3; proteins expressed by humanized cells have a variety of post-translational modifications, such that the humanized collagen type I $\alpha$1 chain has a molecular weight of 138 kDa.

In the present disclosure, the amino acid sequence of the secretion signal peptide from $T.$ $cruzi$ $\alpha$-mannosidase, the amino acid sequence of GFP, and the sequence of TEV protease cleavage site are encoded by a DNA sequence of SEQ ID NO: 4.

Meanwhile, the present disclosure also provides an expression vector of rhCol1A1, including nucleotide sequences of the rhCol1A1 and a basic vector pcDNA3.1.

The present disclosure further provides a method for expressing the rhCol1A1 using a humanized cell protein expression system, including transfecting the expression vector of the rhCol1A1 into host cells to allow expression, where the host cells are Expi293F™ human embryonic kidney cells.

Example 1

Construction of the Expression Vector

The amino acid sequences of the secretion signal peptide from $T.$ $cruzi$ $\alpha$-mannosidase, the GFP protein, and the TEV protease cleavage site were codon optimized and the gene sequence (SEQ ID NO: 4) was synthesized. It was inserted between the Nhe I and BamH I restriction sites of the plasmid pcDNA3.1 to generate a plasmid suitable for secreting and expressing the fusion protein. The gene sequence encoding the amino acid sequence (SEQ ID NO: 2) at positions 162-1,218 of the humanized collagen type I $\alpha$1 chain was synthesized by Sangon Biotech Co., Ltd. and inserted between BamH I and Xho I restriction sites of the plasmid suitable for the fusion protein to obtain an expression vector capable of expressing the rhCol1A1.

Example 2

Expression of rhCol1A1
 (1) Plasmid extraction: the plasmid vector obtained in Example 1 was transformed into $Escherichia$ $coli$ DH5$\alpha$, inoculated into LB broth (each liter of the broth included 10 g peptone, 5 g yeast powder, and 5 g NaCl) to allow incubation at 37° C. and 200 rpm for 30 min; a resulting transformed bacterial solution was spread on an LB agar plate (containing 0.1 mg/mL ampicillin) to allow incubation upside down in an incubator at 37° C. for 12 h. and Positive single colonies were selected and added into 50 mL LB broth (containing 0.1 mg/mL ampicillin) to allow incubation at 37° C. and 200 rpm for 12 h; a plasmids were extracted using a plasmid bulk extraction kit (Beyotime: D0025-3), the concentration of the plasmid was detected using a Nanodrop instrument, and the extracted plasmid was stored at 4° C.
 (2) Protein expression: Expi293F™ cells were subjected to pre-suspension culture in serum-free medium (Genetimes ExCell Bio: HE000-N012) on a shaker at 37° C., 110 rpm, 80% humidity and 7% carbon dioxide. When the cell density reached (1.5-2.5)×$10^6$ cells/mL and the cell viability was greater than 95%, transfection of the Expi293F™ cells was conducted with a plasmid transfection kit (Beyotime: C0518). Specifically, 80 μL of a transfection reagent was added into 1 mL cell medium, and mixed gently to obtain a solution A. Forty micrograms of plasmid was added into 1 mL cell medium, and mixed gently to obtain a solution B. The solution B was gently mixed with the solution A and allowed to stand for 15 min. A mixture of solutions A and B was added to 40 mL of Expi293F™ cells obtained by suspension culture, and the culture was continued for 6 to 7 d. The cells were monitored daily for viability, and collected when the cell viability was below 50%.
 (3) Protein purification: the cell suspension was centrifuged at 11,000 rpm for 10 min at 4° C. An obtained supernatant was incubated with a well-balanced 5 mL nickel column (Thermo Fisher: 88221) and eluted by gravity. The nickel column was washed with 50 mL of PBS solution containing 10 mM imidazole, followed by gradient-elution with PBS solutions containing 30 mM, 50 mM, 100 mM, 200 mM, and 300 mM imidazole separately. The protein was detected by SDS-PAGE. PBS eluate containing the target protein with high purity was combined, and the imidazole was removed by an ultrafiltration tube (Millipore, UFC9010).
 (4) GFP fusion protein excision: the fusion protein was removed with a kit (Beyotime: P2307). GFP-collagen fusion protein in 200 μL of PBS solution was added to 20 μL of enzyme reaction solution, and then 50 U of enzyme solution was added to allow for reaction at 4° C. overnight. Complete reaction was confirmed by SDS-PAGE, where the original protein band disappeared and a new protein band with a small molecular weight appeared. The protein solution was incubated with a nickel column to remove the tagged protein and enzyme, leaving the target protein rhCol1A1 in the penetration solution. As shown in FIG. 1, the protein gel electrophoresis confirmed the presence of rhCol1A1.

Example 3

Determination of rhCol1A1 Activity in Promoting Cell Migration

On the back of a 6-well plate, horizontal lines were evenly drawn with a marker using a ruler, where one horizontal line was drawn every 0.5-1 cm, and 5 horizontal lines were drawn for each well. About $5*10^5$ BALB/c 3T3 cells were added to each well and cultured overnight to allow the cells to adhere. The next day, the cells were streaked with a sterile tip along the ruler, and washed 3 times with PBS to remove the streaked cells. Dulbecco's modification of Eagle's medium (DMEM) (1-2% FBS) was added. A control group and experimental groups with different rhCol1A1 concentrations (10 μg/mL and 100 μg/mL) were set. The cells were returned to the incubator. Sampling and taking photos were conducted at 0 h, 6 h, 12 h, and 24 h. Three photos were taken for each experiment, and scratch areas were analyzed and calculated using ImageJ software to obtain the scratch recovery rate at different times. The calculation was carried out as follows: Recovery rate %=(scratch area at time 0—scratch area at corresponding time)/scratch area at time 0*100. Three independent experiments were conducted and the data were presented as mean±standard deviation. T-test was performed with a significance level of $P<0.05$ (*) and $P<0.01$ (**).

Figure 2:
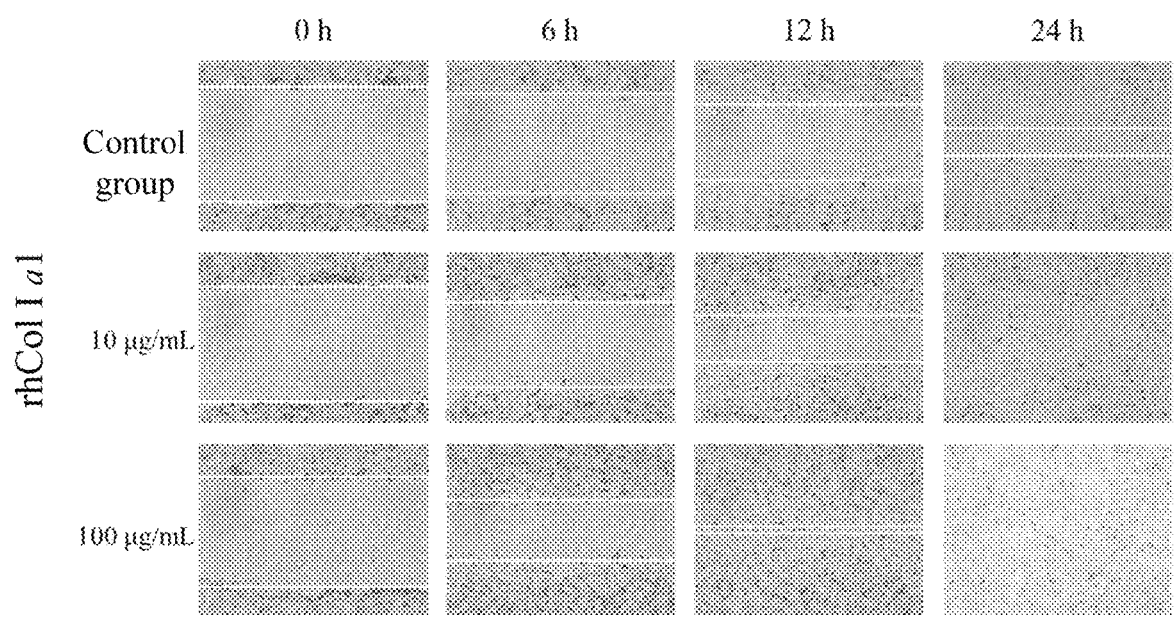
FIG. 2 is a diagram showing the promotion of cell migration by rhCol1A1.
Figure 3:
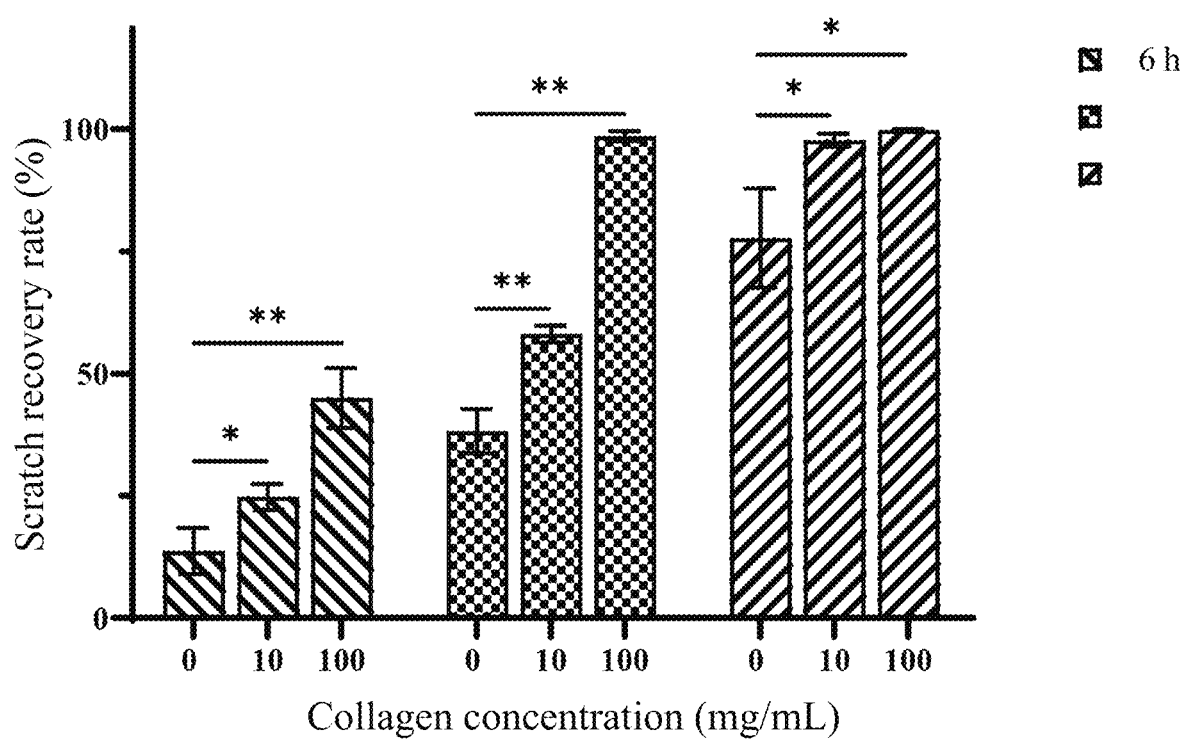
FIG. 3 is graph of showing the static of scratch recovery rate for evaluating the promotion of cell migration by rhCol1A1 of the present disclosure.

As shown in FIG. 2, upon treatment with 10 μg/mL and 100 μg/mL rhCol1A1, the scratches between cells were completely repaired at 24 h. The control without rhCol1A1 still had gaps. Meanwhile, as shown in FIG. 3, compared with the control group without collagen, rhCol1A1 prepared according to the present disclosure had the activity of promoting cell migration at 0 h, 6 h, 12 h, and 24 h, with higher concentrations yielding better effect.

Although the embodiments of the present disclosure have been illustrated and described, it should be understood that those of ordinary skill in the art may make various changes, modifications, replacements and variations to the above embodiments without departing from the principle and spirit of the present disclosure, and the scope of the present disclosure is limited by the appended claims and their legal equivalents.

The present disclosure and the embodiments thereof are described as above, and the description is not limiting. What is shown in the drawing is only one of the embodiments of the present disclosure, and the actual structure is not limited thereto. All in all, if a person of ordinary skill in the art, inspired by the present disclosure, comes up with embodiments similar to the technical solutions without an inventive step, the embodiments, without departing from the purpose of the present disclosure, shall fall within the protection scope of the present disclosure.

---

SEQUENCE LISTING

```
Sequence total quantity: 4
SEQ ID NO: 1            moltype = AA  length = 1060
FEATURE                 Location/Qualifiers
source                  1..1060
                        mol_type = protein
                        note = rhCol1A1
                        organism = synthetic construct
SEQUENCE: 1
GGSQLSYGYD EKSTGGISVP GPMGPSGPRG LPGPPGAPGP QGFQGPPGEP GEPGASGPMG   60
PRGPPGPPGK NGDDGEAGKP GRPGERGPPG PQGARGLPGT AGLPGMKGHR GFSGLDGAKG   120
DAGPAGPKGE PGSPGENGAP GQMGPRGLPG ERGRPGARGP AGARGNDGAT GAAGPPGPTG   180
PAGPPGFPGA VGAKGEAGPQ GPRGSEGPQG VRGEPGPPGP AGAAGPAGNP GADGQPGAKG   240
ANGAPGIAGA PGFPGARGPS GPQGPGGPPG PKGNSGEPGA PGSKGDTGAK GEPGPVGVQG   300
PPGPAGEEGK RGARGEPGPT GLPGPPGERG GPGSRGFPGA DGVAGPKGPA GERGSPGPAG   360
PKGSPGEAGR PGEAGLPGAK GLTGSPGSPG PDGKTGPPGP AGQDGRPGPP GPPGARGQAG   420
VMGFPGPKGA AGEPGKAGER GVPGPPGAVG PAGKDGEAGA QGPPGPAGPA GERGEQGPAG   480
SPGFQGLPGP AGPPGEAGKP GEQGVPGDLG APGPSGARGE RGFPGERGVQ GPPGPAGPRG   540
ANGAPGNDGA KGDAGAPGAP GSQGAPGLQG MPGERGAAGL PGPKGDRGDA GPKGADGSPG   600
KDGVRGLTGP IGPPGPAGAP GDKGESGPSG PAGPTGARGA PGDRGEPGPP GPAGFAGPPG   660
ADGQPGAKGE PGDAGAKGDA GPPGPAGPAG PPGPIGNVGA PGAKGARGSA GPPGATGFPG   720
AAGRVGPPGP SGNAGPPGPP GPAGKEGGKG PRGETGPAGR PGEVGPPGPP GPAGEKGSPG   780
ADGPAGAPGT PGPQGIAGQR GVVGLPGQRG ERGFPGLPGP SGEPGKQGPS GASGERGPPG   840
PMGPPGLAGP PGESGREGAP GAEGSPGRDG SPGAKGDRGE TGPAGPPGAP GAPGAPGPVG   900
PAGKSGDRGE TGPAGPAGPV GPVGARGPAG PQGPRGDKGE TGEQGDRGIK GHRGFSGLQG   960
PPGPPGSPGE QGPSGASGPA GPRGPPGSAG APGKDGLNGL PGPIGPPGPR GRTGDAGPVG   1020
PPGPPGPPGP PGPPSAGFDF SFLPQPPQEK AHDGGRYYRA                       1060

SEQ ID NO: 2            moltype = AA  length = 1057
FEATURE                 Location/Qualifiers
source                  1..1057
                        mol_type = protein
                        note = amino acid sequence at positions 162 to 1,218 of the
                          humanized collagen type I alpha 1 chain
                        organism = synthetic construct
SEQUENCE: 2
QLSYGYDEKS TGGISVPGPM GPSGPRGLPG PPGAPGPQGF QGPPGEPGEP GASGPMGPRG   60
PPGPPGKNGD DGEAGKPGRP GERGPPGPQG ARGLPGTAGL PGMKGHRGFS GLDGAKGDAG   120
PAGPKGEPGS PGENGAPGQM GPRGLPGERG RPGAPGPAGA RGNDGATGAA GPPGPTGPAG   180
PPGFPGAVGA KGEAGPQGPR GSEGPQGVRG EPGPPGPAGA AGPAGNPGAD GQPGAKGANG   240
APGIAGAPGF PGARGPSGPQ GPGGPPGPKG NSGEPGAPGS KGDTGAKGEP GPVGVQGPPG   300
PAGEEGKRGA RGEPGPTGLP GPPGERGGPG SRGFPGADGV AGPKGPAGER GSPGPAGPKG   360
SPGEAGRPGE AGLPGAKGLT GSPGSPGPDG KTGPPGPAGQ DGRPGPPGPP GARGQAGVMG   420
FPGPKGAAGE PGKAGERGVP GPPGAVGPAG KDGEAGAQGP PGPAGPAGER GEQGPAGSPG   480
FQGLPGPAGP PGEAGKPGEQ GVPGDLGAPG PSGARGERGF PGERGVQGPP GPAGPRGANG   540
APGNDGAKGD AGAPGAPGSQ GAPGLQGMPG ERGAAGLPGP KGDRGDAGPK GADGSPGKDG   600
```

```
VRGLTGPIGP  PGPAGAPGDK  GESGPSGPAG  PTGARGAPGD  RGEPGPPGPA  GFAGPPGADG    660
QPGAKGEPGD  AGAKGDAGPP  GPAGPAGPPG  PIGNVGAPGA  KGARGSAGPP  GATGFPGAAG    720
RVGPPGPSGN  AGPPGPPGPA  GKEGGKGPRG  ETGPAGRPGE  VGPPGPPGPA  GEKGSPGADG    780
PAGAPGTPGP  QGIAGQRGVV  GLPGQRGERG  FPGLPGPSGE  PGKQGPSGAS  GERGPPGPMG    840
PPGLAGPPGE  SGREGAPGAE  GSPGRDGSPG  AKGDRGETGP  AGPAGPAGAP  GAPGPVGPAG    900
KSGDRGETGP  AGPAGPVGPV  GARGPAGPQG  PRGDKGETGE  QGDRGIKGHR  GFSGLQGPPG    960
PPGSPGEQGP  SGASGPAGPR  GPPGSAGAPG  KDGLNGLPGP  IGPPGPRGRT  GDAGPVGPPG   1020
PPGPPGPPGP  PSAGFDFSFL  PQPPQEKAHD  GGRYYRA                              1057

SEQ ID NO: 3           moltype = DNA  length = 3171
FEATURE                Location/Qualifiers
source                 1..3171
                       mol_type = other DNA
                       note = DNA sequence encoding the amino acid sequence at
                         positions 162 to 1,218 of the humanized collagen type I
                         alpha 1 chain
                       organism = synthetic construct
SEQUENCE: 3
cagctgtctt atggctatga tgagaaatca accggaggaa tttccgtgcc tggccccatg    60
ggtccctctg gtcctcgtgg tctccctggc ccccctggtg cacctggtcc caaggcttc   120
caaggtcccc ctggtgagcc tggcgagcct ggagcttcag gtcccatggg tccccgaggt   180
ccccaggtc cccctggaaa gaatggagat gatggggaag gtgaaaaacc tggtcgtcct   240
ggtgagcgtg ggcctcctgg gcctcagggt gctcgaggat tgcccggaac agctggcctc   300
cctggaatga agggacacag aggtttcagt ggtttggatg tgccaaaggg agatgctggt   360
cctgctggtc ctaagggtga gcctggcagc cctggtgaaa atggagctcc tggtcagatg   420
ggccccccgtg gcctgcctgg tgagagaggt cgccctggag tcccctgcct tgctggtgct   480
cgtggaaatg atggtgctac tggtgctgcc gggccccctg gtcccaccgg ccccgctggt   540
cctcctggct tccctggtgc tgttggtgct aagggtgaag ctggtccca agggcccga   600
ggctctgaag gtccccaggg tgtgcgtggt gagcctggcc ccctggccc tgctggtgct   660
gctggccctg ctgaaacccc tggtgctgat ggacagcctg gtgctaaagg tgccaatgg   720
gctcctggta ttgctggtgc tcctggcttc cctggtgccc gaggccccct tggacccag   780
ggccccggcg gccctcctgg tccccaagggt aacagcggtg aacctggtgc tcctggcagc   840
aaaggagaca ctggtgctaa gggagagcct ggccctgttg tgttcaagg acccctggc   900
cctgctggag aggaagggaa gcgaggagct cgaggtggtt tccctggcgc agatggttgt  1020
gctggtccca agggtccgc tggtgaacgt ggttctcctg gccctgctgg ccccaaagga  1080
tctcctggtg aagctggtcg tcccggtgaa gctggtctgc ctggtgccaa gggtctgact  1140
ggaagccctg gcagccctgg tcctgatggc aaaactggcc cccctggtcc cgccggtcaa  1200
gatggtcgcc ccggacccc aggcccacct gtgccccgtc gtcaggctgg tgtgatggga  1260
ttccctggac ctaaaggtgc tgctggagag cccggcaagg ctggagagcg aggtgttccc  1320
ggaccccctg gcgctgtcgg tcctgctggc aaagatggag aggctggagc tcagggaccc  1380
cctgcccctg ctggtccgc tggcgagaga ggtgaacaag gccctgctgg ctccccgga   1440
ttccagggtg tccctggtcc tgctggtcct ccaggtgaga caggcaaacc tggtgaacag   1500
ggtgttcctg gagaccttgg cgcccctggc ccctctggaa caagaggcga gagaggtttc   1560
cctggcgagc gtggtgtgca aggtccccct ggtcctgctg gtcccgagg ggccaacggt   1620
gctcccggca acgatggtgc taagggtgat gctggtgccc ctggagctcc cggtagccag   1680
ggcgcccctg gccttcaggg aatgcctggt gaacgtggtg cagctggtt tccagggcct   1740
aagggtgaca gaggtgatgc tggtcccaaa ggtgctgatg ctctcctgg caaagatggc   1800
gtccgtggtc tgaccggccc cattggtcct cctggccctg ctggtgcccc tggtgacaag   1860
ggtgaaagtg gtcccagcgg ccctgctggt cccactgga ctcgtggtgc ccccggagac   1920
cgtggtgagc ctggtcccc cggccctgct ggctttggt gccccctgg tgctgacggc   1980
caacctggtg ctaaaggcga acctggtgat gctggtgcta aaggcgatgc tggtccccct   2040
ggccctgccg accccgctgg accccctggc ccattggta atgttggtgc tcctggagcc   2100
aaaggtgctc gcggcagcgc tggtcccct ggtgctactg gtttccctgg tgctgctggc   2160
cgagtcggtc ctcctggccc ctctggaaat gctggaccc ctggccctc tggtcctgct   2220
ggcaaagaag gcggcaaagg tcccgtggt gagactggcc ctgctggacg tcctggtgaa   2280
gttggtccc ctggtccccc tggccctgct ggcgagaaag gatccctgg tgctgatggt   2340
cctgctggtc ctcctggtac tcccggggcct caaggtattg ctggacagcg tggtgtggtc   2400
ggcctgctgc gtcagagagg agagagaggc ttccctggtc ttcctggccc ctctggtgaa   2460
cctggcaaac aaggtccctc tggagcaagt ggtgaacgtg gtccccctgg tcccatggga   2520
ccccctggat tggctggacc ccctggtgaa tctggacgtg aggggctcc tggtgccgaa   2580
ggttcccctg gacgagacgg ttctcctggc gccaagggtg accgtggtga gaccggcccc   2640
gctggacccc ctggtgctcc tggtgctcct ggtgcccctg gccccgttgg ccctgctggc   2700
aagagtggtg atcgtggtga gactggtcct gctggtcccg tcggtcctgt tggccccgtt   2760
ggcgcccgtg gccccgccgg accccaaggc ccacgtggtg acaagggtga gacaggcgaa   2820
cagggcgaca gaggcataaa gggtcaccgt ggcttctctg gcctccaggg tcccccctggc   2880
cctcctggct ctcctggtga acaaggtccc tctgagcct ctggtcctgc tggtcccga   2940
ggtcccccctg gctctgctgg tgctcctggc aaagatggac tcaacggtct ccctggcccc   3000
attgggcccc ctggtcctcg cggtcgcact ggtgatgctg gtcctgttgg tccccccggg   3060
cctcctggac ctcctggtcc cctggtcct cccagcgctg gttttcgactt cagcttcctg   3120
ccccagccac ctcaagagaa ggctcacgat ggtggccgct actaccgggc t            3171

SEQ ID NO: 4           moltype = DNA  length = 819
FEATURE                Location/Qualifiers
source                 1..819
                       mol_type = other DNA
                       note = DNA sequence encoding the amino acid sequence of the
                         secretion signal peptide from T. cruzi alpha-mannosidase,
                         the amino acid sequence of the GFP, and the sequence of
```

```
                TEV protease cleavage site
                organism = synthetic construct
SEQUENCE: 4
atgagactgc tgaccgccct gttcgcctac ttcatcgtgg ccctgatcct ggccttcagc   60
gtgtccgcca agagcatgca ccaccaccat caccatcatc acatgagcaa gggcgaggaa  120
ctgttcaccg gcgtggtgcc catcctggtg gaactggacg gcgacgtgaa cggccacaag  180
ttctctgtgc ggggcgaggg cgagggggac gccacaaatg gcaagctgac cctgaagttc  240
atctgcacca ccggaaagct gcccgtgccc tggcctaccc tggtcacaac cctgacctac  300
ggcgtgcagt gcttcagcag ataccccgac cacatgaagc ggcacgattt cttcaagagc  360
gccatgcccg agggctacgt gcaagaacgg accatcagct tcaaggacga cggcacctac  420
aagaccagag ccgaagtgaa gttcgagggc gacaccctgg tcaaccggat cgagctgaag  480
ggcatcgact tcaaagagga cggcaacatc ctgggccaca agctggaata caacttcaac  540
agccacaacg tgtacatcac cgccgacaag cagaagaacg gcatcaaggc caacttcaag  600
atccggcaca acgtggaaga tggcagcgtg cagctggccg accactacca gcagaacacc  660
cccatcggcg acggcccccgt gctgctgccc gacaatcact acctgagcac ccagagcgtg  720
ctgagcaagg accccaacga gaagcgggac cacatggtgc tgctggaatt tgtgaccgcc  780
gctggcatca cccacggcga gaacctgtac ttccaaggg                         819
```

What is claimed is:

1. An expression vector for recombinant humanized collagen type I alpha-1 (rhCol1A1), wherein the expression vector for rhCol1A1 is a pcDNA3.1 expression vector comprising the DNA sequence of SEQ ID NO: 4 and the DNA sequence of SEQ ID NO: 3, wherein the rhCol1A1 has the amino acid sequence of SEQ ID NO: 1;

the DNA sequence of SEQ ID NO: 3 is inserted between BamH I and Xho I restriction sites of the pcDNA3.1 expression vector; and the DNA sequence of SEQ ID NO: 4 is inserted between Nhe I and BamH I restriction sites of the expression vector pcDNA3.1.

2. The expression vector according to claim 1, wherein the rhCol1A1 is expressed by a method comprising the following steps: subjecting the human embryonic kidney cells to pre-suspension culture in a serum-free medium on a shaker at 37° C., 110 rpm, 80% humidity, and 7% carbon dioxide; conducting cell transfection when a cell density reaches $1.5 \times 10^6$–$2.5 \times 10^6$ cells/mL and a cell viability of greater than 95%; wherein the cell transfection comprises the following steps: adding a transfection reagent to a first cell medium and mixing gently to obtain a solution A; adding a plasmid containing the rhCol1A1 to a second cell medium and mixing gently to obtain a solution B; adding the solution B into the solution A, mixing gently, and allowing to stand for 15 min; and adding a mixture of the solution A and the solution B into the suspension cultured human embryonic kidney cells, and continuing culture for 6 d to 7 d; when a cell viability reaches lower than 50%, collecting obtained cells for centrifugation to obtain a culture supernatant.

\* \* \* \* \*